US005698774A

United States Patent [19]
Osmanski

[11] Patent Number: 5,698,774
[45] Date of Patent: Dec. 16, 1997

[54] APPARATUS AND METHOD FOR DETERMINING CONCENTRATIONS OF OIL OR OTHER NON-VOLATILE CONTAMINANTS IN CLEANING SOLVENTS

[75] Inventor: Frank A. Osmanski, Hanover Park, Ill.

[73] Assignee: Safety-Kleen Corp., Elgin, Ill.

[21] Appl. No.: 706,003

[22] Filed: Aug. 30, 1996

[51] Int. Cl.⁶ .................................................. G01N 30/90
[52] U.S. Cl. ........................................ 73/61.43; 73/61.54
[58] Field of Search ............................... 73/53.05, 53.06, 73/53.07, 61.41, 61.43, 61.44, 61.54, 61.55, 61.59, 61.62, 61.63, 61.71, 61.72, 64.47; 422/69, 70, 71; 436/169, 170; 210/658

[56] References Cited

U.S. PATENT DOCUMENTS

| | | | |
|---|---|---|---|
| 1,854,143 | 4/1932 | John | 356/70 |
| 1,925,254 | 9/1933 | John | 73/53.06 |
| 2,282,301 | 5/1942 | Petersen | 73/61.71 |
| 2,302,224 | 11/1942 | Jones | 73/53.06 |
| 3,049,964 | 8/1962 | Miller et al. | 73/61.71 |
| 4,004,453 | 1/1977 | Thyrum | 73/61.59 |
| 5,313,824 | 5/1994 | Herguth et al. | 73/53.05 |

*Primary Examiner*—Michael Brock
*Attorney, Agent, or Firm*—James T. FitzGibbon

[57] ABSTRACT

A test apparatus for use in determining the concentration of oils or other soluble contaminants in a petroleum hydrocarbon solvent. The apparatus includes a positioner for a two-layer fibrous sheet, or two separate sheets, in either case providing an upper layer of material that is sorptive to polar materials and a lower layer that is absorptive to non-polar hydrocarbon liquids. When the contaminated liquid evaporates either, as by being heated, a characteristic stain indicative of contaminant level remains on the lower layer. The method includes applying contaminated solvent, separating particulates in the upper fibrous level, and allowing the soluble materials to stain the lower layer. Some embodiments of the apparatus include built-in heating and air circulation means.

29 Claims, 3 Drawing Sheets

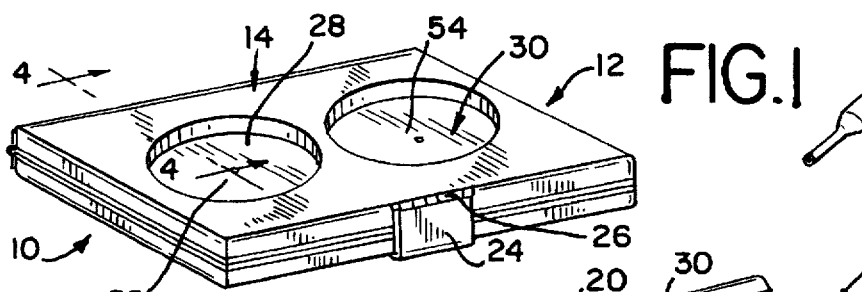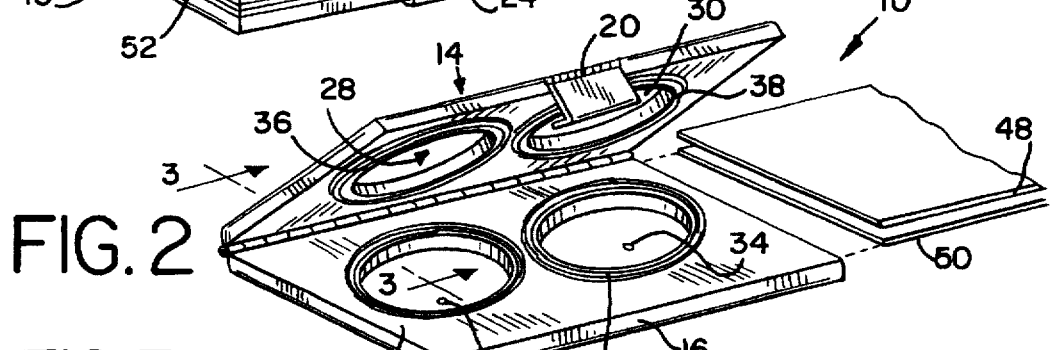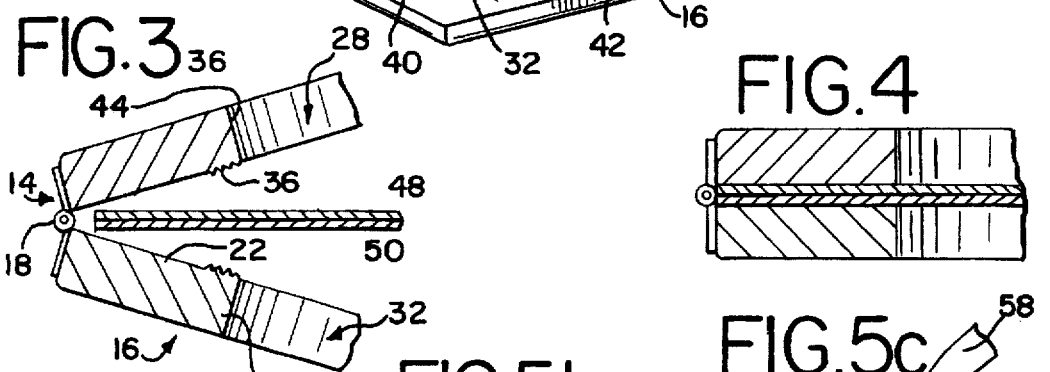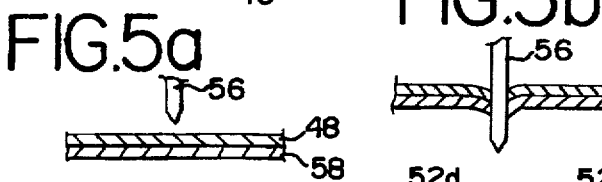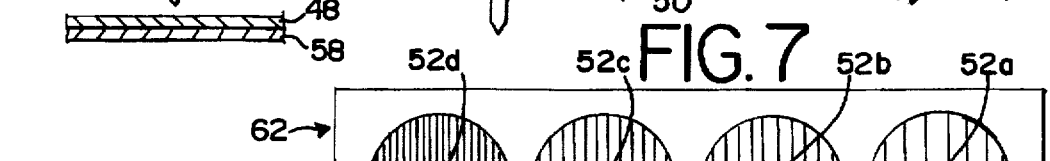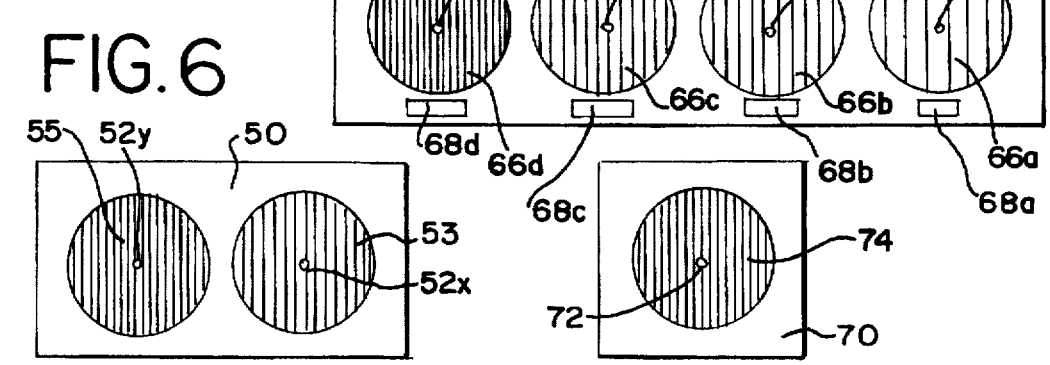

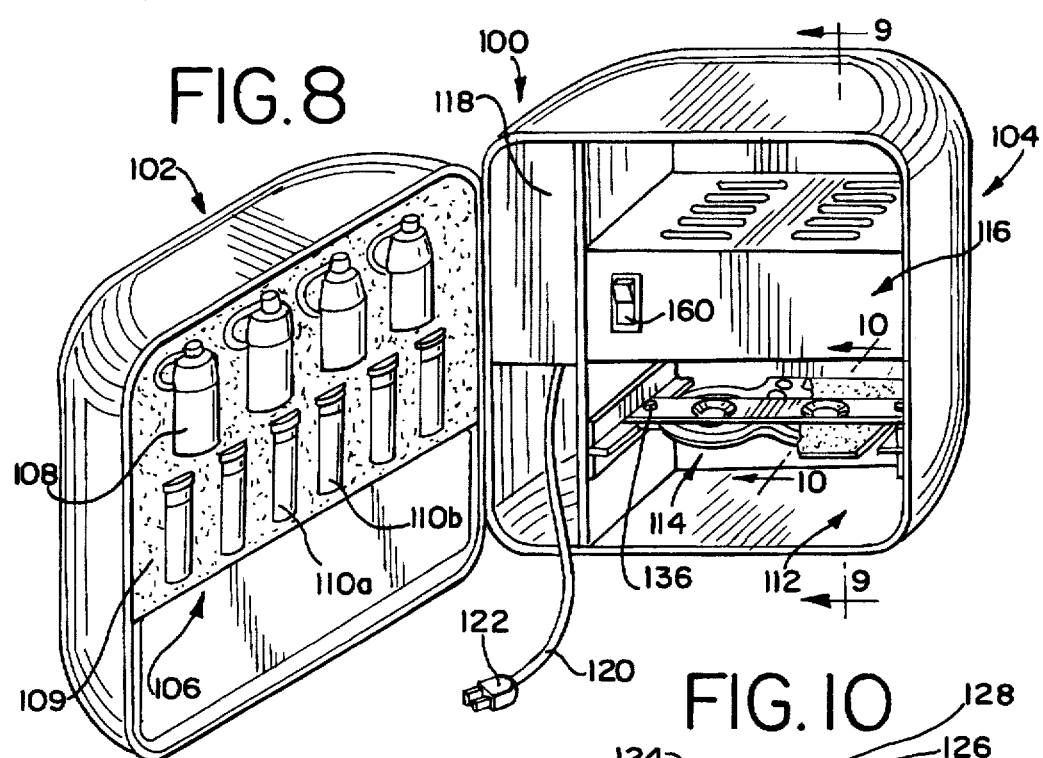
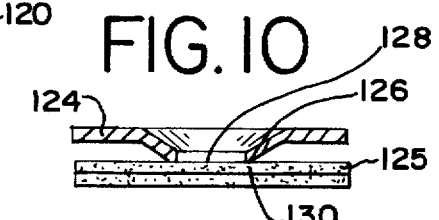
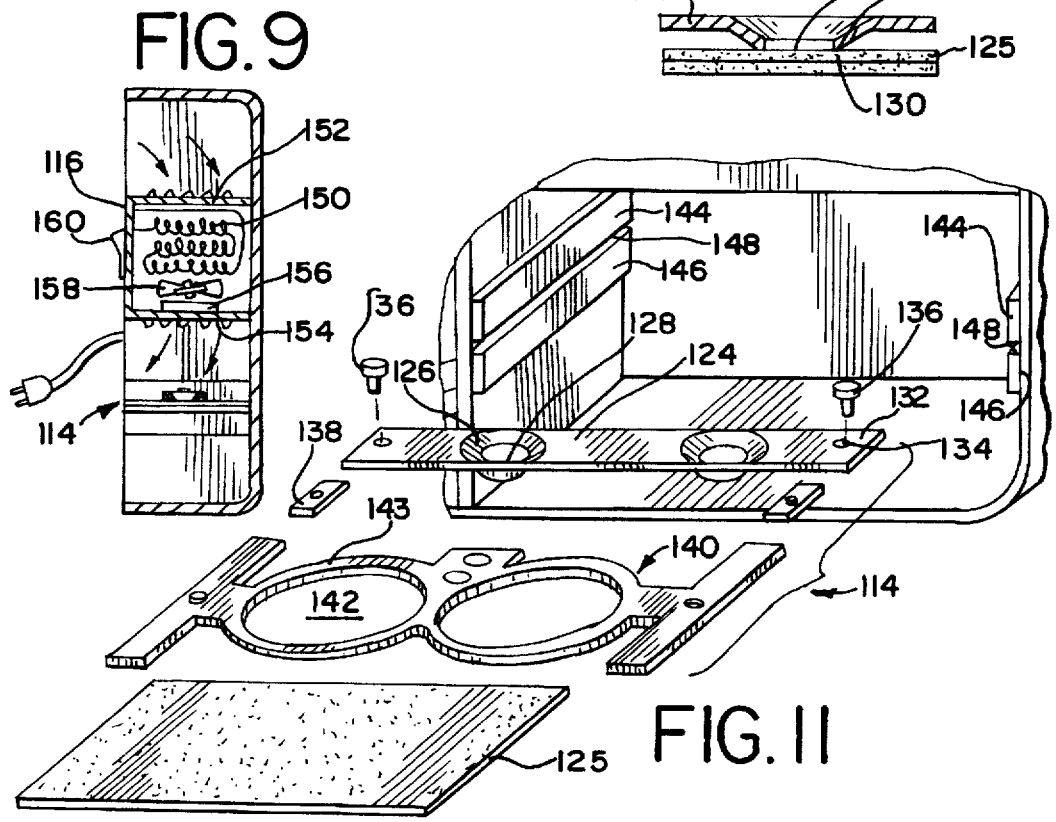

APPARATUS AND METHOD FOR DETERMINING CONCENTRATIONS OF OIL OR OTHER NON-VOLATILE CONTAMINANTS IN CLEANING SOLVENTS

BACKGROUND OF THE INVENTION

The present invention relates generally to methods and apparatus for determining concentrations of oil or other non-volatile contaminants in cleaning solvents, and more particularly to methods and apparatus for such purpose that may be performed by relatively unskilled personnel, in the field, using extremely simple, low-cost equipment.

In its presently preferred form, the invention relates to an apparatus that will provide relatively accurate, on-the-spot determinations of the extent to which solvent used in a parts washer, or like cleaning solvent, such as mineral spirits, has become contaminated with materials, such as lubricating oil and other lubricants, and other soluble contaminants that leave a residue on parts to be cleaned. Materials are normally considered to be contaminants if they have a boiling point beyond the end point of the boiling range distribution of the solvent.

In recent years, methods and apparatus for cleaning mechanical parts, pipes, and other industrial materials of all kinds have changed considerably. Twenty-five or more years ago, mechanics, factory workers and others who had a need to clean mechanical parts often did so merely by taking a pan of gasoline and immersing parts in it, allowing the parts to soak, or scrubbing such parts with a brush until they were acceptably clean. When such a pan of such gasoline, which was commonly used because of its low cost and ready availability, was sufficiently dirty to be considered ineffective, it was simply discarded, either being drained directly into the sewage system or in some cases, mixed with waste oil already destined for disposal by various methods. Needless to say, such practices seriously created fire and explosion hazards, and were environmentally destructive.

With the advent of readily serviceable, safe parts washers, the prior approach to parts washing changed substantially. Hundreds of thousands of service stations, small engine repair shops, factories of all kinds, and other users began employing specially designed apparatus dedicated exclusively to parts washing. Parts washers such as those described in U.S. Pat. No. 3,522,814, which were greatly improved from the standpoint of safety and conservation of materials actually created an industry. Thus, servicing such parts washers by periodically replacing the used solvent at an appropriate time became a self-sustaining business. In later years, industrial products of all kinds, not just mechanical parts or components, have been cleaned in this way in these and similar machines.

The advantages of using such a service included reduction of expenses for equipment purchase, avoiding costs of repair and maintenance, as well as the ability to use a safe solvent with a suitably high flashpoint, customarily mineral spirits or so-called Stoddard solvent. The change in the industry to a service based system wherein used solvent would be periodically picked up and replaced with clean solvent by service personnel immediately overcame environmental difficulties. The new service included picking up used cleaning solvent, replenishing the user's supply with new solvent, and then recycling the dirty, used solvent to reduce cost and environmental damage.

In more recent years, as the price of solvent has continued to increase, and as environmental and conservation concerns continue, significant effort has been directed to insuring that maximum use can be made of existing solvent. In this connection, the economics of using periodically serviceable parts washers are most favorable as long as that the solvent is not changed more often than is really necessary. On the other hand, changes that are too infrequent can create important drawbacks.

In this connection, the need to change solvent arises from two concerns that are not per se related. First, a principal reason for changing used solvent is that the solvent is dirtied by dispersion of particulate matter picked up in the cleaning process. Such solvent can sometimes appear muddy, almost opaque and in some cases appears virtually black to the eye. In some cases, its cleaning effectiveness can be impaired if this is the case.

Sometimes, solvent may be contaminated by color bodies or finely dispersed, but generally harmless, contaminants whereby the solvent visually appears to have lost its effectiveness; however, if such color bodies and finely dispersed contaminants create a misleading appearance of being excessively dirty, it is possible that the solvent might be changed more often than is really necessary.

This problem, together with the problem of dispersed contaminants generally, has been approached and, in some cases, is able to be minimized or eliminated by treating the solvent with additives in such a way that the finely dispersed particulates become more susceptible to agglomeration and settling out. To the extent that such methods are successful, they can prevent false indications that the solvent has used up its effective cleaning capacity and should be replenished.

However, a second class of difficulty with used solvent is that, by reason of the residue on parts being cleaned, the solvent can become excessively diluted with lubricating oil, or other soluble oils, including metalworking fluids, glycol-type materials used as coolants or in automatic transmission fluid ("ATF") or the like. Thus, prior to being washed, mechanical parts are commonly coated with oils, greases or such other fluids as a result of leakage, for example. Normally lubricated internal parts such as bearings, gears, shafts and their housings run in oil, and are almost always oily before being cleaned. In some instances, other kinds of oils or greases may find their way into the cleaning solvent. These constituents, as well as ATF, some coolants or cutting compositions, unlike dispersed particulate matter, are truly soluble in the solvent and are incapable of being removed from the solvent without measures such as fractional distillation.

Herein, and in the claims, such materials are sometimes collectively referred to as "soluble, non-volatile ("NV") contaminants" or simply "contaminants." In other cases, particularly for purposes of brevity in the specification, the term "oil" is simply used in the broad sense to mean such contaminant materials. Regardless of their actual composition, they present equally troublesome challenges.

Consequently, regardless of the extent to which particulate matter has been or may be removed from parts washing solvent, the solvent becomes ineffective when the concentration of such soluble, non-volatile contaminants in the solvent reaches or exceeds a given level. This point will vary somewhat depending on the application; that is, whether the part is to be plated, painted, sand or grit blasted, allowed to dry, or merely preserved with an anti-rust coating. In any case, when solvent contains 20% of such contaminants, it is almost always ineffective; its cleaning effectiveness begins to be compromised at about 2% for some applications and in some cases is impaired significantly at levels of 10–15%, again depending on the application.

For the best balance of performance and economy, therefore, it is desired to change parts washing or like cleaning solvent when the concentration of dissolved contaminants reaches a predetermined level, such as more than 5% to 10%, by way of example, or in some cases, more than 15%. Regardless of what absolute concentration of oil or other contaminant is considered excessive, it is highly desirable to be able to make a comparatively accurate determination of when such level or concentration of the oil or other contaminant has been reached. It is naturally also desirable to be able to make such a determination without incurring significant expense, including the expense or inconvenience of using elaborate testing equipment. Thus, it would be very advantageous if a parts washer service representative, user, or owner were able to go into the field and perform an effective test in almost no time, at virtually no expense.

In particular, it would be even more desirable in the case of a service representative if he were able to test solvent in such a way that the customer-user could view the test and be made aware of the need for service by a visible, easy-to-comprehend demonstration. In the alternative, it would be advantageous if the customer could be made to feel comfortable that his or her existing solvent is capable of further use before a change is required.

In the past, various methods have been suggested for determining the level of particulate contaminants in motor oils, and other methods have been provided for detecting very small amounts, such as 5–100 parts per million (ppm), of oil in water. However, the present invention is directed to determining the level of one soluble component in another, i.e., the concentration of oil or other soluble, non-volatile contaminant in a solvent system, usually a solvent made wholly or in part from mineral spirits. In such a method, according to the invention, rather than determining the level of particulate matter in the mix of solvent and oil as the primary consideration in determining whether the solvent should be replaced, the inventive method provides a method wherein particulate matter and chromophore or color-forming bodies are removed from the mix of contaminant and solvent so as not to create a false or misleading end point. Thereupon, as a part of the same process, the mix is tested for relative concentrations of contaminant in the solvent.

The prior art having failed to provide a practical, low-cost method of determining the relative concentration of oil or other soluble, non-volatile contaminants in parts washing or other cleaning solvents, it is an object of the present invention to provide an improved apparatus and method for such purpose.

Another object of the invention is to provide a test method which requires a minimum of components, all inexpensive, and which is highly reliable in use.

Yet another object is to provide a test method which is simple and repeatable enough to be effective when used in the field by relatively unskilled personnel.

A further object of the invention is to provide a test apparatus which includes a frame or the like for holding a pair of fibrous sheets in contact with each other, with the sheets being of a particular composition so that one sheet sorbs color bodies and filters or entraps particulate matter, and the other sheet creates a residual, post-drying stain indicative of the concentration of the oil or other soluble contaminant in the solvent being tested.

Yet another object of the invention is to provide a test method wherein, after color bodies and particulate matter are effectively removed by one fiber layer from a specimen of solvent containing oil, the solvent phase is evaporated and the residual amount of oil in the other fiber layer is presented as a visible stain, the appearance of which is measured against a standard of known concentration.

A further object of the invention is to provide a test wherein the tested specimen may be compared against another specimen prepared by using the same apparatus and method, or against a previously prepared standard. Such a reference standard may, in a broad sense, be an effective reference, such as a photo or representation of other solvents, or actual specimens of materials in various states or degrees of contamination.

A still further object of the invention is to provide an apparatus which uses two layers of fibrous material, one preferably being a layer "loaded" or impregnated with a sorptive material such as silica gel, and the other being a posterboard paper layer, with the upper or silica gel layer being adapted to pick up color bodies and particulates and the lower or posterboard layer being adapted to diffuse a mixture of non-polar solvent and non-polar oil or other soluble contaminant within it.

Another object of the invention is to provide a test method wherein, once a paper or fibrous sheet has been wetted by and has absorbed a specimen of solvent containing oil or other soluble contaminant, localized heating is used to evaporate the solvent phase so as to leave an oily, non-volatile residue having a characteristic color and optical density that can be compared to a standard to effectively determine the concentration of oil in the solvent with a significantly high degree of accuracy to reduce the unnecessary expense of premature solvent replacement.

A further object of the invention is to provide a method as described above wherein initial localization and ultimate dispersion of the oil within the papers may, in some cases, be accomplished by forming a rough-edged hole in the two overlying or superposed specimen papers or fiber layers.

A still further object of the invention is to provide a method using treated fibrous sheets such as papers or the like, one containing a silica gel material and the other being a posterboard or like material, with the method including piercing the two adjacent or superimposed sheets so as to create, in effect, a silica gel lining within the posterboard opening, thus insuring that particulates in the non-volatile oil or the like entering the lower layer have already been entrapped or filtered by the silica gel in the upper fibrous layer.

An additional object of the invention is to provide a test apparatus which includes a holder for positioning two fibrous sheets in overlying or superposed relation, with the first or upper fibrous sheet acting as a filter for particulates and being impregnated with a material for sorbing color bodies from solvent, and a second or lower fibrous sheet for absorbing a solvent-oil mixture, whereby, when a small specimen of the solvent-oil mixture is deposited on the sheets and the solvent is evaporated, the upper sheet has retained color bodies and particulates and the lower sheet displays a visible stain characteristic of the oil concentration in the solvent/oil specimen.

Another object is to provide an apparatus as just described wherein a portion of the apparatus outlines adjacent but separate areas for forming the spot.

Yet another object of the invention is to provide a test method and apparatus using a two layer, single fibrous sheet having a layer that acts as a particulate filter and is sorptive of color bodies and a lower layer that absorbs non-polar hydrocarbons.

Still another object of the invention is to provide an integrated test kit that includes receptacles for specimens, a heat source, a forced air delivery system and a specimen holder capable of presenting adjacent surfaces for comparing materials having known and unknown oil-in-solvent contents, respectively.

A further object of the invention is to provide a test kit which includes a convenient specimen holder that is extensible to receive a specimen paper and which is retractable to a position of use adjacent the outlet of a hot air circulation system.

A still further object of the invention is to provide a test kit which includes all the materials necessary to perform the analytical steps of the method of the invention.

An additional object is to provide a test kit which includes a system for heating air adjacent the specimen and circulating the air over the specimen by a fan or the like.

Another object of the invention is to provide a test kit wherein the heat source for evaporating solvent from a fibrous specimen paper consists of a heated plate positioned beneath and in contact with the fibrous test sheet.

Yet another object of the invention is to provide a test kit for determining the comparative oil-in-solvent or soluble, non-volatile concentration of an unknown specimen relative to a specimen of known concentration, which includes a heated plate for warming the fibrous sheet and a fan for improving air circulation in the vicinity of the specimen.

A further object of the invention is to provide one or more test kits or apparatus for such a method wherein rings having portions in snug contact with the paper specimen serve to confine the liquid specimen being deposited for the test to a pre-determined area on the fibrous multi-layer sheet.

The foregoing and other objects and advantages of the invention are achieved in practice by providing a test apparatus which includes a frame for positioning at least one sheet providing a fibrous substrate layer treated with a material for filtering or entrapping particulates and for sorbing chromophoric groups, and a second layer positioned immediately beneath and in contact with the first layer and being adapted to absorb non-polar oily materials, with the frame preferably presenting at least two separate target areas, one for placement of the liquid specimen to be analyzed and the other for a standard.

The objects are also achieved by providing a method of determining the relative concentration of lubricating oil and similar soluble contaminants within a cleaning solvent comprising at least a major portion of mineral spirits, such method including the steps of positioning two layers of fibrous material in overlying relation, wetting a given spot on the material, allowing one layer to filter or entrap particulates and sorb color-forming bodies and the other layer to be wetted, after which the wetted areas are dried and the residual stains are compared to determine the relative concentration of oil that had been dispersed in the contaminated solvent.

The manner in which the foregoing and other objects and advantages of the invention are achieved and practice will become more clearly apparent when reference is made to the following detailed description of the preferred embodiments of the invention set forth by way of example and shown in the accompanying drawings, wherein like reference numbers indicate corresponding parts throughout.

BRIEF DESCRIPTIONS OF THE DRAWINGS

FIG. 1 is a perspective view of the test apparatus of the invention, showing a frame in the closed position, holding two sheets of fibrous material in overlying relation in preparation for performing the test;

FIG. 2 is a perspective view of the apparatus of FIG. 1, showing the same in an open position, with a pair of sheets about to be positioned in the frame unit;

FIG. 3 is a vertical sectional view of the apparatus, taken along lines 3—3 of FIG. 2, showing the apparatus slightly open and with the fibrous sheets in position to be clamped in place by the frame;

FIG. 4 is a sectional view similar to that of FIG. 3, taken along lines 4—4 of FIG. 1 and showing the frame in the closed position;

FIGS. 5a–5c are elevational views, partly diagrammatic in nature, showing a sequence of some of the steps in the method of the invention;

FIG. 6 is a diagrammatic plan view of a test sheet of the invention after use;

FIG. 7 is a plan view of a single test sheet after use and showing the sheet being compared to a previously prepared standard sheet; and FIG. 8 is a perspective view of a self-contained kit providing the apparatus necessary to carry out the test method of the invention;

FIG. 9 is a vertical sectional view, taken along lines 9—9 of FIG. 8 and showing the motor and fan, heating coils and specimen holder of the apparatus of FIG. 8;

FIG. 10 is an enlarged fragmentary vertical sectional view, taken along lines 10—10 of FIG. 8, and showing details of the specimen holder;

FIG. 11 is an exploded perspective view showing the relation of a fiber specimen to the elements of the specimen holder;

DESCRIPTION OF THE PREFERRED EMBODIMENTS OF THE INVENTION

Figure 12:
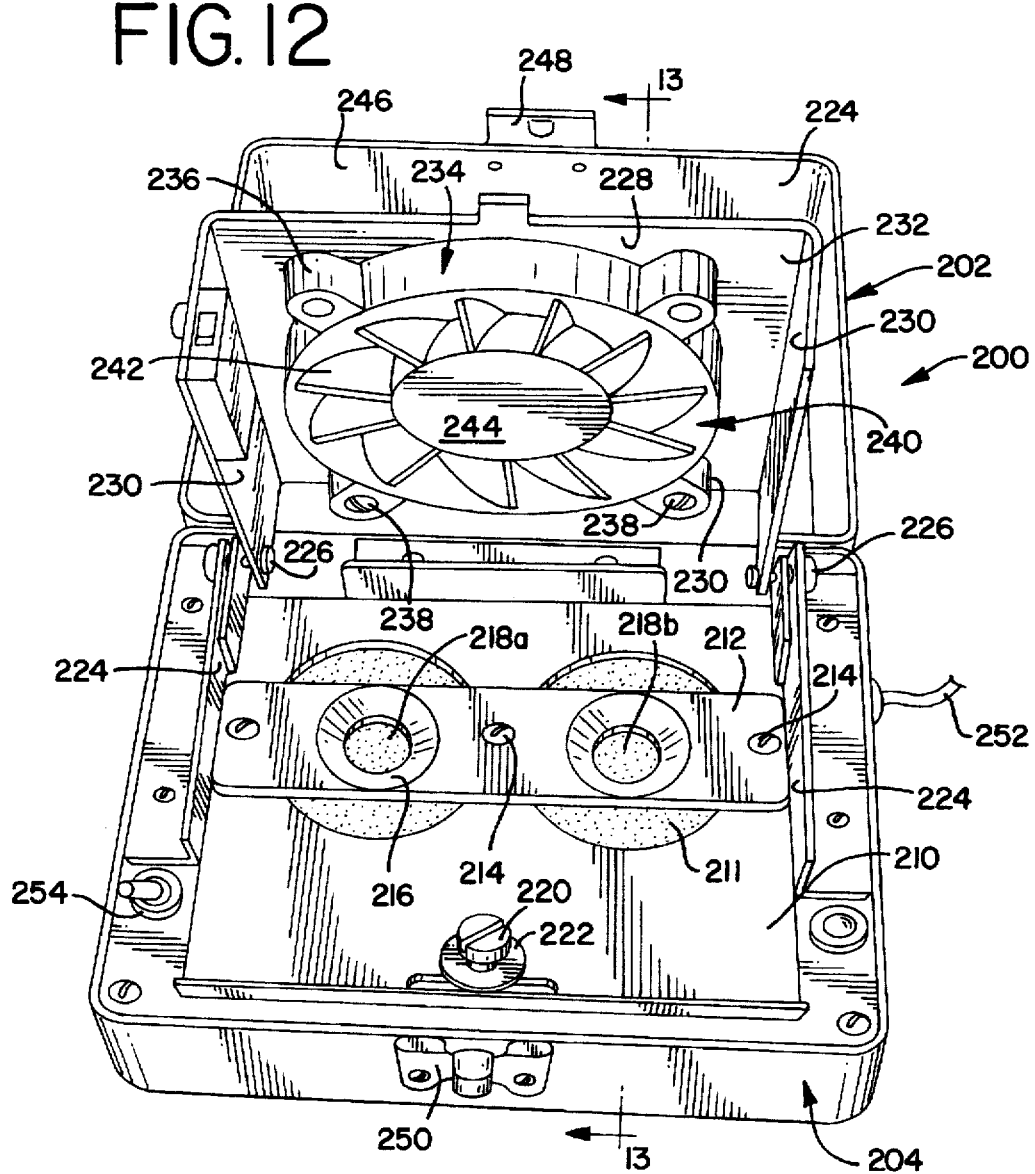
FIG. 12 is a perspective view of another embodiment of test kit made according to the invention; and, FIG. 13 is a fragmentary vertical sectional view, taken along lines 13—13 of FIG. 12 and showing the essential components of that form of test kit.

While the principles of the invention may be applied to somewhat different apparatus, and there may be variations in the exact materials used in the practice of the invention, a description of a few preferred embodiments of the invention will be given for purposes of illustrating what is presently believed to be the best mode of practicing the inventive concept.

Referring now to the drawings in greater detail, and particularly to FIGS. 1 and 2, there is shown one very simple form of apparatus generally designated 10 that is adapted to the practice of the invention. As shown in FIGS. 1–2, the apparatus 10 comprises a sheetholder generally designated 12 and shown to include a top plate generally designated 14 and a bottom plate generally designated 16. The plates 14, 16 are pivotally attached to each other as by a piano hinge 18 that joins opposed counterpart outer margin portions 20, 22 of the plates 14, 16 together.

As is also shown in FIGS. 1 and 2, latch means in the form of a clasp 24 attached by a hinge 26 to the top plate 14 insures that, when desired, the top and bottom plates 14, 16, remain together.

In one preferred form of the apparatus of the invention, a pair of access openings generally designated 28, 30 are formed in the top plate 14 and these openings register with counterpart bottom openings 32, 34 in the bottom plate 16. As shown in FIGS. 2–4, serrated inner margins 36, 38 are disposed adjacent the openings 28, 30 and similar serrated margins 40, 42 are provided in the lower plates 16. The openings 28, 32, for example, are shown to be formed (FIGS. 3–4) by upper and lower sidewalls 44, 46 in the plates 14, 16.

FIGS. 3 and 4 show in detail only one pair of openings, 28, 32, it being understood that the other openings 30, 34 are identical in construction and operation. While the dimensions of the sheetholder 12 are not crucial to the practice of the invention, a typical frame has two openings and measures 3.5 inches by 2 inches. A center opening of about 1 to 1.25 inches has been found to operate satisfactorily.

Referring again to FIGS. 1–4, and assuming it is now desired to use the test apparatus 10 of the invention, the clasp 24 is manipulated so as to permit the plates 14, 16 to be opened to the position shown in FIG. 2. Thereupon, upper and lower fibrous sheets, 48, 50 are placed in generally overlying relation and positioned with their margins in approximate registration with the outer edges of the plates 14, 16. The plates 14, 16 are then closed, moving from the position of FIG. 3 to that of FIG. 4. In this portion (FIG. 1) the spring steel clasp 24 is locked and retains the two plates 14, 16 in snug overlying relation under spring tension. At this point, the serrations 36, 38, 40, 42 comprising opposed upper and lower circular opening margins of the respective plates 14, 16 have snugly engaged the sheets 48, 50, ensuring that they are in an extremely closely superposed or overlying relation. For reasons which will appear, it is highly desirable that the two paper sheets remain so positioned.

As referred to above, the upper fibrous sheet 48 is preferably made from a paper resembling filter paper and "loaded" or impregnated throughout its body with a finely subdivided silica gel material. One material that has proven advantageous in the practice of the invention is identified as a silica gel loaded absorbent paper, having a thickness of 0.008 to 0.010 inches and is made by the Whatman Company and identified in their catalog as paper "No. SG81". Preferably, a rectangular specimen is used, being cut into a 2 by 3 inch size.

The lower sheet of fibrous material generally designated 50 is a light to medium yellow colored posterboard material, approximately 0.015 inches in thickness, One specimen that has proven very effective was obtained from the Royal Lace Company of Garwood, N.J. This paper material 50 is also cut into identical 2×3 inch rectangles so that the two fibrous sheets are substantially the same size.

While two separate sheets of the different kinds just described are appropriately used, it is also possible to obtain a single sheet having two layers, with the upper layer having the function of its counterpart sheet 48 and the lower layer having a function equal to its counterpart sheet 50. Hence, herein and in certain claims, the expression "layer" may be taken as meaning the same as the expression "sheet", depending on the manner in which these functions are presented.

After the sheet or sheets have been positioned in the superposed relation and locked in the sheet holder 12, it is desired to form a center openings 52, 54 in the generally central portions of the exposed papers lying within the openings 28, 30 in the holder 12. For this purpose, a medium to large nail 56, preferably one having a shank diameter of approximately 0.105", is used to form center openings or holes 52, 54 in the two exposed center portions of the sheets.

Thereupon, using a small, preferably disposable pipette generally designated 58, a small specimen 60 of a control solvent/oil mix and a small specimen 60 from the used cleaning solvent being sampled are each withdrawn, and a two drop sized specimen 60 of each is placed in each of the openings 52, 54 formed by the nail 56. Each drop ordinarily having a volume of 0.045 ml, each specimen is therefore preferably approximately 0.09 ml. Upon contact with the superposed paper sheets, the specimens wet both layers of paper 48, 50. Of course, more or fewer drops may be used, as referred to below.

The tester/observer may then note that the upper layer sorbs various color bodies and filters or entraps whatever particulates are in the specimen, leaving the residue, which consists essentially of a mixture of the petroleum solvent and an unknown concentration of oil or other soluble, non-volatile contaminant, to diffuse into both sections of the fibrous paper sheets. The test specimens are allowed to soak into the papers 48, 50 for a short time, at present preferably being one to one and one-half minutes. Because of the action of the silica gel-impregnated paper, the color bodies and the particulates are taken up only by that layer.

Thereupon, both spots on the lower layer or sheet are dried using suitable means such as an ordinary hair drier, typically of 1500 watts capacity, set on a high setting for a period of two minutes. A "heat gun" or the equivalent may also be used. This time is selected so as to be sufficient to effectively evaporate all of the solvent, leaving an oily residue in the lower layer or paper, and particulates and color bodies in the upper layer or paper. The holder is then opened and the layers are observed. The optical density of the oily spot on the lower or posterboard layer is then compared with that of the dried solvent/oil stain on the control.

FIG. 6 shows a bottom view of the lower paper 50 (or lower paper layer) having spots or residue areas 53, 55 surrounding the nail holes 52x, 52y. The left-hand area 55 is shown as being darker than the right-hand or standard area 53, thus indicating that the concentration of oil or other contaminant is higher than that of the standard.

Using the above-described test, when 2% or less oil is in the solvent, the concentration of the residual oil is such that the oil spot is barely visible on the yellow posterboard paper. Beginning at about 5%, the optical density of the spot becomes definitely visible and gradually becomes increasingly dark until its color is extremely pronounced at a 15% concentration, appearing very dark and moist in contrast to the surrounding paper.

In the foregoing examples, two drops of a 0.045 ml of volume were used.

Those skilled in the art will appreciate that amounts of contamination that are permissible in one particular application would not be permissible in another application, and that the tests can be tailored to provide the most desirable response. For purposes of use in parts washer solvent of the type currently used by Applicant, two drops of 0.045 ml volume have proven satisfactory and able to provide reasonable discrimination in a range of 2% to 15% contaminant oil concentration.

While the upper paper layer is used primarily to remove chromophores and particulate material to insure that such materials do not interfere with or adversely affect the accuracy of the reading indicative of the oil concentration, the level of particulate material may also permit a fairly accurate estimate of the level of suspended solids in the solvent. However, as pointed out, the principal purpose of the test is to measure the concentration of dissolved oil in the specimen rather than the particulate level.

In the example just discussed, the preferred method includes using a standard which is at or near the borderline of acceptable oil concentration for the particular application of the customer rather than using pure solvent as the standard. Accordingly, when the control specimen is made up, it might include oil at a concentration of 5%, which would indicate that a change is recommended or should be considered. Where the actual test specimen spot appears less dense than the control, the solvent has significant remaining useful life. If the spot appears darker and more oily than the control, then a change is indicated. If an oil free solvent specimen is used as the control, the test will indicate the presence of oil, but since the decision to change solvent is based on the assumption that a certain amount of oil is acceptable, and will inevitably be present even in solvent that has only been used for a short time, the test is intended to distinguish between a concentration which contains measurable amounts of oil but is still acceptable and a concentration which is high enough to compromise cleaning effectiveness. Therefore, the control specimen might contain between 2% and 7% oil, preferably 5%, merely by way of illustration.

Referring now to another embodiment of the invention, FIG. 7 shows a color test chart generally designated 62 and shown to be in the form of an elongated sheet 64 having plural image or spot areas 66a, 66b, 66c, and 66d, for example. Each spot may, but need not have a nail hole or like opening 52a, 52b, etc. therein. The optical density of the spots varies, increasing, for example, towards the left margin of the sheet 64. A plurality of legends 68a, 68b, etc. are provided, each displaying a numerical indication of the concentration of solvent associated with the particular spot. Using this test method, a test paper 70 is provided having a center opening 72, and after having been treated with a solvent/oil specimen and after the solvent has evaporated, the paper 70 will present an image or stain area 74. When the operator performs the test, which is performed in all respects as with its counterpart described above, except that only one test spot is made, the test specimen is compared against the standard sheet 64 to determine which stain appears closer to the test spot and thus estimates the concentration of oil in the solvent.

Regarding the alternate method, the same kind of paper is used, while the holder preferably has only a single opening, inasmuch as the standard need not be prepared as a part of the test.

The formation of the holes 52, 54, etc. is a sometimes preferred although not strictly necessary step in keeping with the practice of the invention. This hole is believed to provide several advantages. First, using an instrument such as the nail serves to create a thin layer of silica gel and paper fibers that extend into and along the sidewalls of the opening. This insures that the oil-solvent mix passing into the paper fibers from that area has an opportunity to contact the silica gel or other sorptive material before passing into the posterboard or lower layer.

While the test is operative without forming the center opening, such a practice tends to localize the oil drop and regularize the shape of the spot.

The form of sheetholder 12 illustrated includes two adjacently disposed openings, although it is apparent that a single opening may be used if only a single specimen is to be tested, or several individual tests are to be performed in sequence. A specimen holder having a hinge action for opening is described, although it is understood that any frame having other parts movable between open and closed positions will be effective in practice of the invention. Such constructions include, but are not limited to upper and lower holders aligned by posts for parallel opening and closing movement, for example. The only requirement for the holder is that it be able to position the test sheet for insertion of the specimens and closable to a position wherein the specimens are held in tightly overlying relation.

In the foregoing description, the expressions "sorbs" or "sorptive" have been used as generic expressions to describe the action of the silica gel on the materials in the oil/solvent mix. The expressions "chromophores" and "color bodies" as used herein are essentially synonymous, meaning whatever organic compositions are present to create color in the solvent-oil mix. These are usually complex molecules having particular groups within in them that form characteristic colors and are generally highly polar in nature. Because high specific surface materials such as silica gel enables it to sorb significant quantities of strongly polar materials such as color bodies, the generic expression "sorb" is used to include adsorption, absorption or chemisorption. While silica gel is preferred, other generally similar materials that display the proper sorptive characteristics in relation to the highly polar molecules in the oil may be used.

Regarding the lower layer of paper or other fibrous sheet 50, a posterboard paper described has proven satisfactory in use. This paper should preferably be a rather dense paper but one that is permeable to solvent and oil, and not treated as with a clay or other hard surface coating. Such material readily absorbs non-polar materials intimately such as the solvent and oil, which are truly soluble or miscible in each other in all proportions.

The pipette 58 used to obtain the specimen contains a thin wall bulb portion and an extended, small diameter shank with a lumen or opening extending centrally therethrough. Such pipettes are extremely inexpensive and disposable so that a different one may be used with each test.

As pointed out above, the invention may be practiced in various forms. Where the user of the process travels from location to location, and may encounter a variety of conditions, the use of a self-contained test kit providing all the equipment and comparative specimens necessary to make an oil-in-solvent determination may be used.

Thus, and referring now to FIGS. 8–11, there is shown an alternate form of test kit generally designated 100. This assembly 100 includes a cover unit generally designated 102 and a main housing portion generally designated 104. The cover 102 includes an insert generally designated 106 preferably of a preformed cellular material and containing plural preformed pockets 108 having flexible sidewall portions 109 for accommodating a plurality of standard bottles 110a, 110b, etc. with two rows of vials being shown. Preferably, five or six standard-containing bottles are appropriately used, each having a known concentration of oil, i.e., 5%, 7%, 10%, 15%, etc. in a solvent.

The main housing unit 104 preferably includes an outer shell generally designated 112, a specimen holder assembly generally designated 114 and a heater/blower shroud unit generally designated 116. A power supply portion 118 occupies an upper corner of the shell 112 and a power cord 120 terminating in a plug 122 supplies power, preferably 110 v AC power, to the heater/blower positioned behind the shroud 116.

A specimen holder 114 recessed within the housing 104 is shown to include an upper plate 124 having beveled margins 126 defining circular openings 128 with sharp lower edges 130 (FIG. 10). The outer margins 132 of the upper plate 124 include openings 134 for fasteners 136 adapted to secure the spacers 138 to a lower plate generally designated 140 and shown to include enlarged apertures 142 having generally circular frames 143. A multi-layer paper specimen 125 is positioned in use atop the lower plate 140 and beneath the upper plate 124 where the lower edges 130 of the openings 128 are in snug, interfering fit relation with the specimen sheet 125. In the preferred form of apparatus, the upper and lower guide bars 144, 146 define therebetween a slot 148 in which the specimen holder assembly 114 moves for inserting and removing the fiber or paper specimens, as will appear.

Referring now in particular to FIG. 9, it is shown that heater coils 150 of the resistance wire type are provided between the upper and lower louvered panels 152, 154. The lower louvered panel 154 positions a miniature motor 156 that operates a blower or fan 158 under the control of a switch 160 (FIG. 8). As shown by the arrows, the fan causes warm air to flow through the upper and lower louvered panels 152, 154 where there temperature is significantly raised. This air then flows downwardly and over the specimen 125 positioned in the holder assembly 114.

The method of the invention is similar to that described above in that, when a specimen is ready to be analyzed, the specimen holder 114 is pulled to an extended position relative to the slot 148. A specimen sheet 125 is inserted between the upper and lower plates 124, 140 where it is snugly positioned by reason of being sized for an interference fit. Thereupon, two drops or other control quantity of liquid are deposited through the openings 128 defined by the beveled margins 126, and these drops wet a spot on the paper whose spread is initially confined by the sharp edges of the openings 128. These openings are sometimes called "focusing rings" in that they insure a localization of the liquid within the specimen paper.

As indicated above, one of the openings 128a receives two drops of the field specimen and the other opening 128b receives two drops of a liquid selected from one of the standard bottles 110a, 110b, etc. Preferably, the bottle is labeled with a known concentration of oil in solvent and presumably contains a target concentration relative to which the field specimen is to be compared. Thus, if the user desires not more than 15% oil within the solvent, a specimen bottle or test tube having such a concentration is available for selection and comparison purposes.

The self-contained unit including the provision of the motor, fan, and heating coils is a convenient and inexpensive way to eliminate random factors such as positioning of the dryer unit or the like. If desired, a timer may be placed in series with the motor switch to insure maintenance of standard tests conditions.

Figure 13:
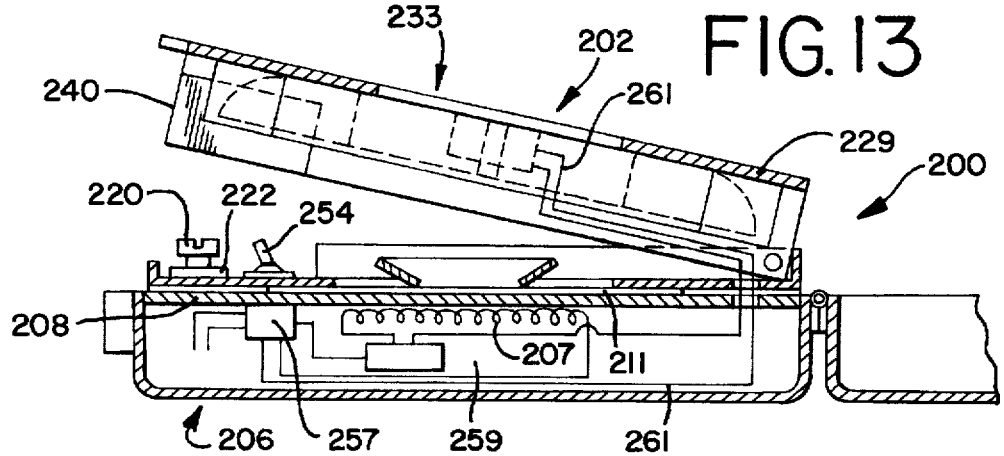

Referring again to the concept that a suitable apparatus may be made in various forms, FIGS. 12 and 13 show a further modified form of test kit generally designated 200. FIG. 12, which is a perspective view, shows the test kit 200 includes a combination cover and fan carrier assembly generally designated 202 and a base assembly generally designated 204. The base assembly 204 includes several principal components including a bottom shell generally designated 206 and shown to include bottom and sidewall portions, and to support a heating plate 208 containing an electrical resistance heating coil 207 (schematically shown) of a known type.

Spaced just above the heating plate 208 by a working clearance substantially equal to the thickness of a paper specimen sheet is an apertured specimen holddown plate 210. In FIGS. 12 and 13, the sheet is shown as 211. The holddown plate 210 is surmounted by a ring carrier plate 212 secured thereto by fasteners 214. Beveled margins 216 define "focusing rings" or openings 218a, 218b in the plate 212, through which access may be had to the paper specimen 211. The holddown plate 210 is secured in position over the heating plate 208 by a fastener 220 and a force-diffusing element such as a washer 222. The fastener may be of the quarter-turn type if desired for convenience. Other suitable latching mechanisms may be used if desired.

In order to permit the holddown plate 210 to be raised and lowered for purposes of inserting a specimen sheet 211, the holddown plate 210 is secured by pivot arms 224 lying to either side of the plate 210 and is movable about pivot pins 226 which extend through openings in the arms 224. Ordinarily, the holddown fastener and washer are held captive relative to the plate. Raising the plate, when desired, is simply a matter of imparting a quarter turn or more to the fastener and lifting the plate, which pivots about the axis of the pins 226.

Referring now to the cover and fan carrier assembly generally designated 202, this unit is shown to comprise in turn, a motor carrier frame generally designated 228, and a cover shell 229. The carrier frame 228 includes opposed substantially identical side rails 230 forming downturned margins of a motor support plate 232 having a center opening generally designated 233, beneath which a spider generally designated 234 is positioned. A plurality of mounting ears 236 form an outer part of the spider 234 and have suitable openings to receive fasteners 238 secured to the support plate 232.

A fan assembly generally designated 240 is shown to include a plurality of blades 242, and a housing 244 for a motor (not shown). The outer cover or shell 229 includes bottom and sidewall portions and has a front wall 246 containing a pivotable clasp 248 adapted to mate in use with a lower latch 250. A power cord 252 supplies current to the switch 254. In the preferred form, a portion of the switch 255 includes a dual function timer 257 having one of its output leads 259 connected to the heating coil 207 and the other output lead 261 connected to one terminal of the motor. In the preferred form, therefore, after the switch 254 is actuated, a period of one minute elapses before the heating coil 207 is energized. This permits the solvent and the oil or other contaminant to be absorbed in the paper sheet 211. At a predetermined later time, such as one minute after the heating coil is energized, a second pair of contacts within the timer is closed and this energizes the fan motor. The timer may be programmed or pre-set to achieve the desired delay periods, and may optionally "clock out" so as to turn off after a predetermined time.

Under this preferred arrangement, after the drops of liquid, such as those taken from the pipette 58, are deposited within the openings 218 in the focusing rings and wet the paper 211, the switch 254 is thrown. The timing sequence permits the liquid to be absorbed for a controlled time, the heat to begin to be applied for a given time, and the fan motor to be energized thereafter as long as the switch remains closed. When the specimen appears to be dry, the switch is again turned off and the specimen holddown plate 210 is lifted by manipulating the holddown screw 220. Thereafter, the paper sheet or sheets may be removed for inspection and comparison of the standard to the unknown.

In a preferred form, appropriate safety interlocks of a type known to those skilled in the art may be provided so that only when the cover and fan carrier 202 are in position of use over the plate and the paper will the fan motor and the heater be energized.

While the structure of the test kit 200 just described is significantly different from that of its counterpart test kit 100, the function of the two devices is similar in that, in each, a two layer paper specimen is placed between a "focusing ring" or the like and a support plate to localize deposition of the oily solvent to be tested. Thereupon, a heating means is energized and fresh air is circulated to facilitate evaporation of volatile organic constituents (VOC) from the paper that has sorbed the non-polar, oily materials. The residue after drying is a spot that is analyzed or inspected visually to determine the oil content of the solvent, using other oily materials or a test chart.

According to the invention, a relatively accurate, low-cost quantitative test is provided. The test may not only assist in making an informed decision as to when to change parts washing solvent or the like and demonstrate the condition of the solvent to the user or other observer, for example. Parts washing solvent has been used as an example, but it will be understood that there are other materials wherein it is advantageous to be aware of the concentration of one undesirable non-polar material within another for various purposes, and the principles and the apparatus of the present invention may be employed for such purpose.

It will thus be seen that the present invention provides a novel apparatus and method having a number of advantages and characteristics including those pointed out herein and others which are inherent in the invention. Two preferred embodiments having been described in detail by way of example, it is apparent that variations and modifications to these described forms of apparatus and method may be made without departing from the spirit of the invention or the scope of the appended claims.

I claim:

1. A test apparatus for use in determining the approximate concentration of soluble, non-volatile contaminants in a petroleum hydrocarbon solvent, said apparatus comprising, in combination, a fibrous sheet positioner, said positioner having opposed sheet-engaging portions adapted to receive and position a test sheet within the apparatus, said sheet engaging elements including portions defining at least one opening for exposing selected portions of a fibrous sheet having at least two layers, said first and second layers being disposed in use in closely overlying relation within said positioner, said first layer being an upper layer made from a fibrous material impregnated with a material that is sorptive to polar materials and acts as a filter relative to dispersed particulate contaminants, and said second layer being a lower layer that is absorptive of non-polar organic hydrocarbon liquid materials, said opening being constructed and arranged so as to permit application of sensible heat to said sheet in order to evaporate said petroleum hydrocarbon solvent from said lower layer and to leave a non-volatile residue to produce a characteristic stain that is comparable to a standard to determine the concentration of oil in said solvent.

2. A test apparatus as defined in claim 1, wherein said material that is sorptive to polar contaminants is silica gel.

3. A test apparatus as defined in claim 1, wherein said fibrous layer that is absorptive of non-polar hydrocarbons is a posterboard paper.

4. A test apparatus as defined in claim 1, wherein said at least one opening comprises a pair of adjacently disposed openings each defined by inner sidewalls in said opposed portions of said positioner.

5. A test apparatus as defined in claim 1, wherein said sheet positioner comprises upper and lower, generally rectangular frame elements joined by a hinge along opposed outer margins, and wherein said at least one opening comprises a pair of openings.

6. A test apparatus as defined in claim 1, wherein said at least two layers of said fibrous sheet comprises a first sheet and a second sheet, said first sheet being impregnated with silica gel and being from about 0.005 to about 0.015 inches in thickness and wherein said second sheet is a sheet of posterboard paper of about 0.010 to about 0.020 in thickness.

7. A test apparatus as defined in claim 1, wherein said at least one opening is defined by opposed facing margins of said positioner, and wherein at least one of said margins has a serrated surface so as to facilitate gripping said sheets.

8. A test apparatus as defined in claim 1, wherein at least a portion of said sheet engaging portion of said positioner includes serrations so as to facilitate gripping said sheets.

9. A test apparatus as defined in claim 1, wherein said opposed sheet engaging portions comprises upper and lower frame elements, wherein said at least one opening comprises a pair of openings, each of said openings being defined by circular sidewalls forming a part of said upper and lower frame elements, and wherein said upper and lower frame elements each including margins surrounding said sidewalls and lying in opposed facing relation, each of said margins having a textured, sheet-gripping surface forming a part thereof.

10. An apparatus as defined in claim 1, which further includes a heat source and an air circulation source adapted to direct heated air to said sheets under the control of an operator.

11. An apparatus as defined in claim 1, which further includes a heated plate positionable in intimate heat exchange relation with said fibrous sheet in order to evaporate solvent to produce said characteristic stain.

12. An apparatus as defined in claim 1, wherein said soluble, non-volatile contaminant is a lubricating oil.

13. An apparatus as defined in claim 1, wherein said soluble, non-volatile contaminant is a lubricating oil and a glycol coolant.

14. A method of determining the approximate concentration of lubricating oil in a hydrocarbon solvent, said method comprising providing a fibrous material having at least two layers in intimate contact with each other, said two layers including a first upper layer comprised of fibers impregnated with a surface active, finely divided material that is sorptive to polar color bodies capable of filtering finely divided particulate materials, and a second, lower layer comprising a material that is absorptive of non-polar solvents and oils, wetting a given area of said fibrous material with a specimen of an oil/solvent mix, allowing the oil/solvent mix to be sorbed by said fibrous material, applying sensible external heat to said layers until substantially all of said solvent has evaporated from said lower layer and comparing the appearance of said given area wetted by said oil/solvent mix to a pre-determined visual standard to determine the differences between the coloration of said given area of said lower sheet and the coloration of said standard.

15. A method as defined in claim 14, wherein said at least two closely overlying layers of fibrous material comprise two separate sheets of material in overlying relation positioned with said first and second layers in intimate contact with each other.

16. A method as defined in claim 14, wherein said two layers comprise two layers of a single fibrous sheet.

17. A method as defined in claim 14, which includes piercing said upper and lower layers so as to form upper and lower, coaxially arranged openings in said layers, and thereafter depositing said specimen of said oil/solvent mix into said openings.

18. A method as defined in claim 14, wherein said upper layer of said fibrous material is impregnated with silica gel.

19. A method as defined in claim 14, wherein said lower layer of said fibrous material is made from a posterboard paper.

20. A method as defined in claim 14, wherein said wetting said given area of said fibrous material comprises wetting said fibrous material at a pair of adjacently disposed areas, and wherein one of said pair of areas is wetted by an oil/solvent mix having a known oil concentration and the other area is wetted by an oil/solvent mix having an unknown oil concentration, and wherein the degree of coloration of said two areas are compared to each other.

21. A method as defined in claim 14, wherein said fibrous material is in the form of a sheet, and wherein said sheet is inserted into a sheet positioner having upper and lower, generally rectangular frame elements joined by a hinge extending along opposed outer margins of said frame elements.

22. A method as defined in claim 14, wherein said upper layer comprises a layer impregnated with silica gel and is from about 0.005 to about 0.015 inches in thickness.

23. A method as defined in claim 14, wherein said second layer is a layer of a posterboard paper of about 0.010 to about 0.020 in thickness.

24. A method as defined in claim 14, wherein said predetermined visual standard is a single color stain produced prior to performing said steps of wetting said fibrous material and applying heat thereto.

25. A method as defined in claim 14, wherein said predetermined visual standard comprises a plurality of previously prepared stains, each having a different coloration and each corresponding to a known concentration of oil in said oil/solvent mix.

26. A test kit for use in determining the concentration of lubricating oil in a hydrocarbon solvent, said test kit including a housing, a sheet positioner disposed within said housing and including upper and lower holders spaced apart by a distance substantially equal to the width of a two layer test sheet to be positioned between said holders, a test sheet received between said holders, said test sheet having at least two layers in closely overlying relation, one of said two layers being an upper layer made from a fibrous material impregnated with a material that is sorptive to polar materials and acts as a filter relative to dispersed particulate contaminants in said solvent, and the other of said two layers being a lower layer that is absorptive of non-polar organic hydrocarbon liquid materials, each of said holders providing at least one access opening whereby an oily specimen may be deposited therethrough and onto said sheet, said kit further including a source for heating the air adjacent said sheet and for circulating said heated air over said sheet to evaporate solvent therefrom.

27. A test apparatus for use in determining the approximate concentration of soluble, non-volatile contaminants in a petroleum hydrocarbon solvent, said apparatus comprising, in combination, a fibrous sheet positioner, said positioner having sheet-engaging portions adapted to receive and position a test sheet within the apparatus, said sheet engaging elements including portions defining at least one access area for exposing selected portions of a fibrous sheet having at least two layers, said first and second layers being disposed in use in closely overlying relation when secured by said positioner, said first layer being an upper layer made from a fibrous material impregnated with a material that is sorptive to polar materials and acts as a filter relative to dispersed particulate contaminants, and said second layer being a lower layer that is absorptive of non-polar organic hydrocarbon liquid materials, said access area being constructed and arranged so as to permit application of sensible heat to said sheet in order to evaporate said petroleum hydrocarbon solvent from said lower layer and to leave a non-volatile residue to produce a characteristic stain that is comparable to a standard to determine the concentration of oil in said solvent.

28. A test apparatus as defined in claim 27, wherein said contaminants include lubricating oil.

29. A test apparatus as defined in claim 27, wherein said contaminants include lubricating oil and a glycol coolant.

* * * * *